United States Patent
Appel et al.

(10) Patent No.: US 6,280,395 B1
(45) Date of Patent: Aug. 28, 2001

(54) SYSTEM AND METHOD FOR DETERMINING MUSCLE DYSFUNCTION

(75) Inventors: Gerald David Appel; Harry Wellington Clark, both of Los Angeles; Mary Kathleen Day, Santa Monica, all of CA (US)

(73) Assignee: MPR Health Systems, Inc., Culver City, CA (US)

( * ) Notice: Subject to any disclaimer, the term of this patent is extended or adjusted under 35 U.S.C. 154(b) by 0 days.

(21) Appl. No.: 09/488,208

(22) Filed: Jan. 19, 2000

(51) Int. Cl.[7] ....................................... A61B 5/04
(52) U.S. Cl. ..................... 600/546; 600/587; 600/595
(58) Field of Search ............................... 600/546, 597, 600/587, 595, 594

(56) References Cited

U.S. PATENT DOCUMENTS 5,505,208   4/1996  Toomim et al. .
6,047,202 * 4/2000  Finneran et al. ................... 600/382

OTHER PUBLICATIONS

James H. Graham, Adriana Espinosa, Computer Assisted Analysis of Electromyographic Data in Diagnosis of Low Back Pain, 1989 Nov. 14, 1989 Nov. 17, p. 1118–11123 (PICYE3).

* cited by examiner

Primary Examiner—Eric F. Winakur
Assistant Examiner—Pamela Wingood
(74) Attorney, Agent, or Firm—Lyon & Lyon LLP

(57) ABSTRACT

A system and method for determining back muscle dysfunction comprises data collection and data analysis elements. The system collects electrical muscle activity measurements by applying a plurality of electrodes in a pattern across a patient's or test subject's back, measuring the electrical activity at each of the electrodes and storing the measurements. One or more normative or examined patient databases comprising measurements and results from a number of individuals are used for comparison against the patient's measurements. A patient's back muscle activity is characterized by collecting electrical muscle activity measurements for the patient and comparing an analysis of the patient's electrical muscle activity to the results of the normative or previously examined group.

43 Claims, 9 Drawing Sheets

ABNORMAL MUSCLE PATTERNS

OVERALL PATIENT ACTIVITY DURING THE MPR EVALUATION

MUSCLE SYMBOLS
⊕ HYPERACTIVE MUSCLE
⊟ HYPOACTIVE MUSCLE
◇ RELATED NORMAL MUSCLE

MUSCLE GROUPS TESTED,
LEFT (L) AND RIGHT (R)
CP = CERVICAL PARASPINAL
UT = UPPER TRAPEZIUS
MT = MIDDLE TRAPEZIUS
TP = THORACIC PARASPINAL
LD = LATISSIMUS DORSI
OB = OBLIQUE
LP = LUMBAR PARASPINAL

RIGHT ARM OVERHEAD
LEFT LEG BACK

LEFT ARM OVERHEAD
RIGHT LEG BACK

ARMS OVERHEAD

FORWARD ARM FLEXION
TO 90 DEGREES

ARM ABDUCTION
TO 90 DEGREES

SHOULDER SHRUG

FORWARD BOW
TO 45 DEGREES

TRUNK ROTATION LEFT

TRUNK ROTATION RIGHT

SYSTEM AND METHOD FOR DETERMINING MUSCLE DYSFUNCTION

The present invention relates generally to the field of muscle performance evaluation systems. More particularly, the present invention relates to the field of determining back muscle dysfunction.

BACKGROUND OF THE INVENTION

One method of analyzing the state of a muscle is to collect measurements of electrical signals associated with the activity of that muscle. This type of measurement is known as electromyographic (EMG) measurement, and it may be performed using either invasive (percutaneous) or non-invasive techniques. EMG measurements have been used in a number of different medical applications including the treatment and possible diagnosis of lower back pain.

While percutaneous EMG techniques have been accepted in medicine as accurate for measuring the electrical activity of an underlying muscle, their use is often undesirable or unacceptable. That is, percutaneous EMG techniques require additional materials and expertise, and they present risks not found with non-invasive techniques.

Alternatively, evaluating muscle activity using non-invasive or surface EMG (sEMG) measurements has attracted interest from scientists and medical practitioners for the last 30 years with its promise as an objective, painless muscle measurement technique.

Measurements of surface electrical activity, or any other clinical measurement, must meet several objectives and criteria relating to reliability in order to be considered useful for providing diagnostic or evaluative information. For example, the electrical activity signal measured should be objectively defined and reproducible. The information obtained should meet a need that is best met by making surface EMG measurements. Further, the information should be usable and easily interpreted by the level of skill of practitioners for which it is intended. Finally, the process should be cost-effective and have universal application as either an assessment or therapeutic system or both.

To meet these objectives, the evaluation system should reliably differentiate between healthy, normal, pain-free subjects and subjects with muscle disorders. The evaluation system should also report results with an extremely high level of statistical certainty.

Of the many possible applications for surface EMG measurement, back function evaluation is one of the most suitable. A relatively large percentage of the population experiences back pain that could be attributed to soft tissue damage, i.e., muscle dysfunction. Traditional evaluation techniques have not been effective at objectively determining muscle dysfunction responsible for such pain.

Typical clinical evaluation techniques have relied upon subjective evaluations by the patient to determine the nature of the dysfunction. That is, the patient is usually asked to perform certain motions, and depending upon the patient's ability to perform these motions within subjective pain parameters, a diagnosis is made.

Further, from an economic standpoint, a large percentage of insurance claims are made by individuals claiming to have muscle back pain. Because of the subjective nature of the testing, these claims usually cannot be objectively verified. Accordingly, there is a large potential for fraudulent claims being filed at a substantial cost to insurance companies and ultimately, the consuming public.

A muscle assessment system should be a capable of making significant comparisons of any given patient to a normative group. Because of the comparative nature of the assessment process, the importance of having an evaluation system capable of producing reproducible data becomes paramount.

In the past, studies that have attempted to achieve reproducibility, or to minimize the variation in data, used the maximum voluntary contraction (MVC) method of normalization. This technique requires high levels of muscle activation, causing the engagement of fast-twitch motor units not ordinarily activated in normal movements. That is, these studies compare the measured muscle activity during evaluation to an MVC.

In normal muscle, the slow-twitch motor units produce most of their fused tension before fast-twitch motor units begin to add to muscle force. The addition of fast-twitch motor units in MVC causes a disproportionate increase in the sEMG. The inclusion of fast-twitch motor units, which are seldom used in everyday functioning, occurs with the MVC condition and influences the anatomical distribution and force-voltage relationship of EMG data. Moreover, MVC runs the risk of exacerbating pain and doing further damage to dysfunctional muscles.

Clinical use of sEMG has failed to produce a sufficiently objective evaluation of muscle health. In much of the literature relating to back muscle evaluation, equivalence is sought between EMG resting levels and painful muscles or back pain in general. However, static resting measurements are greatly influenced by small postural adjustment that cannot be adequately controlled. Accordingly, the postural and instrumental error can become so large so as to obscure useful information.

Accordingly, a need exists for a system and method that correctly characterizes muscle dysfunction with a high degree of reproducibility. Further, such a system and method should allow for normalization of data using normally activated muscle values.

U.S. Pat. No. 5,502,208, entitled "Method for Determining Muscle Dysfunction," issued to Toomin et al. ("the '208 patent") and incorporated herein by reference, discloses a method and system that seeks to achieve the above objectives. However, the method and system disclosed in the '208 patent features several disadvantages.

The method disclosed in the '208 patent employs a process that discretely quantifies all of the data elements under analysis. One disadvantage of this method is that it cannot account for data that falls short of subjectively predetermined cutoff points, regardless of the proximity to those cutoff points or the consistency of the data that falls beneath a cutoff point.

For example, the method disclosed in the '208 patent would be indifferent to the following hypothetical case: Out of 100 data elements total, if 50 of them have achieved between 80% and 90% of the predetermined cutoff point, but only ten of them exceeded the cutoff point, then the former 50 data elements would simply be labeled "normal," and discarded from further analysis. Those 50 data elements would not contribute to the final result, despite their close proximity to the cutoff point and their significant number, i.e., their consistency. The system would then use only ten out of 100 elements to make its determination.

The method and system disclosed in the '208 patent is also vulnerable to measurement error. By using discrete quantification, this method allows for opportunities for measured data to fall on one side of the cutoff points on one occasion, and to fall on the other side of the cutoff points if measured on a different occasion, potentially yielding very different results for each occasion.

Moreover, the method and apparatus disclosed in the '208 patent presents its ultimate finding in a broad classification system, wherein each muscle under diagnosis is assigned one of a handful of categories in this classification system: "normal," "symptomatic," "dysfunctional," etc. These terms are only defined as being relative to one another. For example, "symptomatic" is considered more severe than "normal," and "dysfunctional" is more severe than "symptomatic." However, this classification system presents no true or absolute indication of the degree of departure from an ideal or absolute normal condition of the muscle under evaluation.

Another disadvantage of the apparatus disclosed in the '208 patent is that it uses adipose corrections provided from a table, the contents of which depend upon an adipose tissue measuring device that has since been found to be somewhat unreliable.

Another further disadvantage of the method and apparatus disclosed in the '208 patent is that it relies heavily on an assumed normal or Gaussian distribution of data within the normative database. This method is therefore susceptible to error arising from departures from a normal distribution in the actual data collected and analyzed.

SUMMARY OF THE INVENTION

The principal object of the present invention is to provide an improved method and system for determining back muscle dysfunction.

Another object of the present invention is to provide a method and system for determining back muscle dysfunction that employs a method of continuous quantification of all data elements that are collected.

Another object of the present invention is to provide a method and system for determining back muscle dysfunction that presents the results of the diagnostic procedure using a numerical impairment index for each muscle evaluated, whereby the numerical impairment index falls along a continuum of deviation from an ideal normal state for that muscle.

Another object of the present invention is to provide a method and system for determining back muscle dysfunction that employs regression-based formulas to determine adipose corrections necessary for each patient, based on various anatomical measurements of that patient.

Another object of the present invention is to provide a method and apparatus for determining back muscle dysfunction that does not presume the existence of a normal or Gaussian distribution for collected data.

Additional objects and advantages of the invention will be set forth in part in the description that follows, and in part will be evident from the description, or may be learned by the practice of the invention. These and other objects and advantages of the invention may be realized and obtained by means of the instrumentalities, procedures, and combinations particularly pointed out in the appended claims.

To achieve the objects in accordance with the purpose of the invention, as embodied and described herein, a preferred method for determining back muscle dysfunction comprises the steps of: (1) selecting a set of sites on the subject for sensing muscle electrical activity, (2) making electrical activity measurements for the set of sites; and (3) performing an analysis of the electrical activity measurements, the analysis including determining from the electrical activity measurements analysis values for each of a set of muscles and determining from the analysis values a degree of departure from a normal condition, where the degree of departure for the analysis values is normalized with respect to the plurality of muscles.

BRIEF DESCRIPTION OF THE DRAWINGS

The accompanying drawings, which are incorporated in and constitute a part of the specification, illustrate one embodiment of the invention and, together with the description, serve to explain the principles of the invention.

DESCRIPTION OF THE PREFERRED EMBODIMENTS

Reference will now be made to one or more present preferred embodiments of the invention, examples of which are illustrated in association with the accompanying drawings.

Figure 1A:
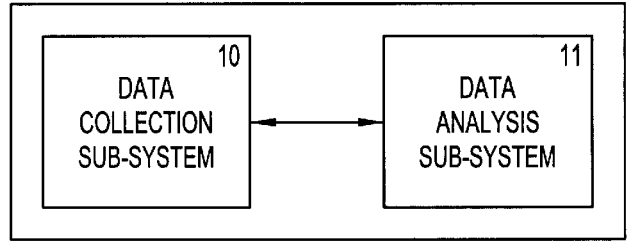
FIG. 1A is an illustration of a preferred embodiment of a back muscle dysfunction system of the present invention comprising a data collection subsystem and a data analysis subsystem.

A preferred embodiment of the system and method for determining back muscle dysfunction is practiced using the back muscle dysfunction (BMD) system 8 illustrated by way of example in FIG. 1A. While the preferred embodiments of the BMD system 8 and method for muscle dysfunction analysis are described in reference to back muscle dysfunction, it is understood that the present system is also applicable to other muscles and muscle groups, such as, for example, leg or abdominal muscles. The basic elements of the BMD system 8 preferably include a data collection subsystem 10 and a data analysis subsystem 11. The BMD system 8 is preferably implemented by separating the functional elements of collection and analysis because of a practical preference to allow for data collection at one location and data analysis at another location. However, the BMD system 8 is optionally implemented in one location wherein elements of the BMD system 8 that aid in the performance of data collection also perform data analysis. Thus, the communication link depicted in FIG. 1A between the two subsystems 10, 11 is optionally unnecessary or is internal to the processing architecture of the BMD system 8.

Figure 1B:
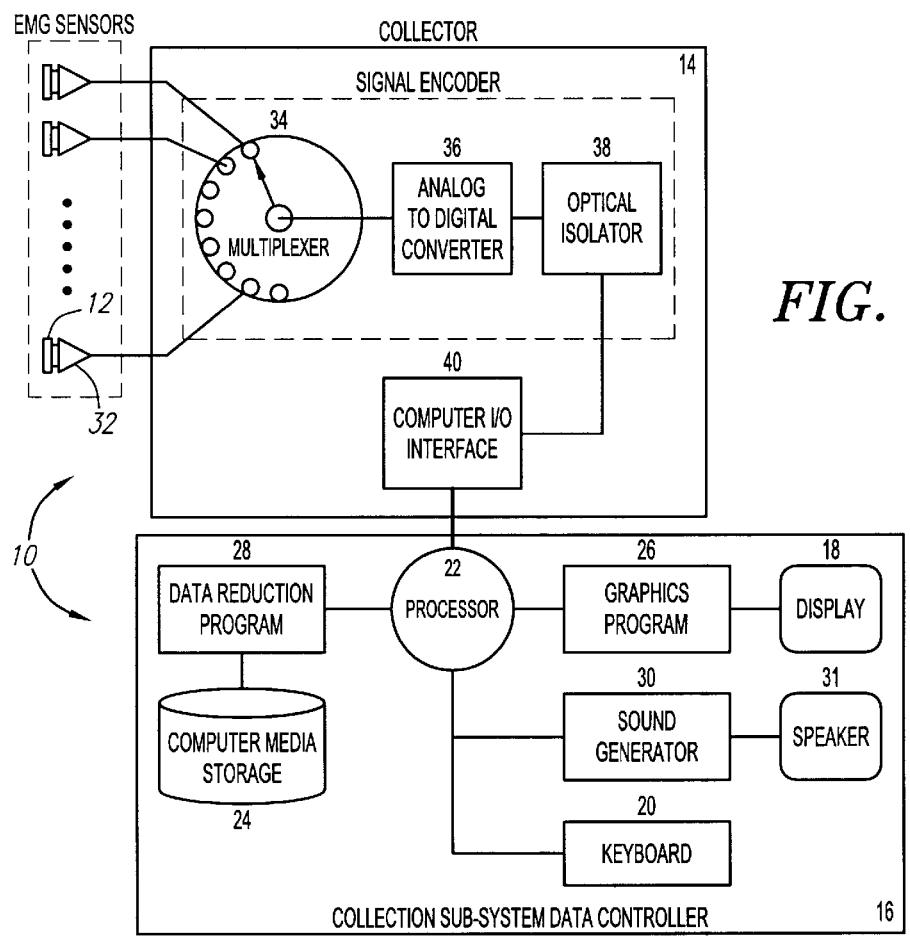
FIG. 1B is an illustration of a preferred embodiment of a data collection subsystem in the back muscle dysfunction system of the present invention.

FIG. 1B details preferred elements of the data collection subsystem 10. The data collection subsystem 10 includes a set of electrodes 12, a collector 14, and a collection subsystem data controller 16. The electrodes 12 are electromyographic surface electrodes, which contact the surface of an individual's skin. Each of the electrodes 12 includes two contacts across which electric potential is measured. The electrodes 12 detect electrical activity changes, i.e., voltage changes between the two contacts of each electrode. Typically, the detected magnitude of electrical activity is in the range of 0–500 microvolts.

The measurement of electric potential changes (electrical activity) on the surface of an individual's skin generated by underlying muscles (sEMG) is performed at each of the plurality of electrodes 12. While sEMG is preferably used to obtain the electrical activity measurements in the preferred data collection subsystem 10, muscle activity is equivalently measured by alternative techniques to sEMG without departing from the spirit and scope of the present invention. Moreover, alternative electrode configurations are also contemplated which correspond to equivalents known in the art. For example, single-contact type electrodes are alternatively used which measure electric potentials with reference to a single common ground, or reference voltage.

The collector 14 preferably includes a signal encoder 60 and a computer I/O interface 40. Voltage detected by the electrodes 12 is transmitted to the signal encoder 60. Prior to transmission to the signal encoder 60, detected analog electrical signals are amplified at the electrodes 12. Preferably, the individual on-electrode amplifier circuitry 32 amplifies the signals detected from the electrodes 12 into a desired voltage range. In a preferred embodiment, the voltage range is zero to four volts. Once the signals from the electrodes 12 are amplified, the signal encoder 60 preferably receives as input amplified analog electrical signals from multiple channels. The signal encoder 60 then preferably digitizes the analog signals, transforms the electrical signals into light signals, and yields as output to the computer I/O interface 40 a digitally encoded light signal along a single optical conduit. The signal encoder 60 also supplies power to operate the on-electrode amplifier circuitry 32. An additional contact is preferably applied in order to cancel common mode variations for the signals detected by the electrodes 12. That is, a common mode drive electrode (not shown) is attached to the patient's back.

To perform these functions, the signal encoder 60 preferably includes a multiplexer 34, an analog-to-digital converter 36, and an optical isolator 38. The amplified analog signals are fed to the multiplexer 34, which selects each of the signals in turn. Each selected signal is then transmitted to the analog-to-digital converter 36. The analog-to-digital converter 36 then converts the received analog signal into a digital signal.

The electrodes 12 and signal encoder 60 are optically isolated from the rest of the data collection subsystem 10 to protect any patient with whom the electrodes 12 are in contact. Thus, there exists no direct electrical connection between the electrodes 12 and the output signal from the collector 14. In the preferred embodiment, the optical isolator 38 is located after the analog-to-digital converter 36. In another preferred embodiment, the optical isolator 38 is realized via a fiber optic cable, which transmits the digital signal from the analog-to-digital converter 36 to the data controller 16 via the computer I/O interface 40. In addition to potentially protecting a patient from shock, the transmission of data using an optical signal though the optical isolator 38 is immune to contamination from environmental electrical or RF interference. Alternatively, instead of the optical isolator 38, another device for electrically insulating the patient from the rest of the data collection subsystem 10 is implemented including using an infrared, radio or another wireless mechanism for communicating measurement data.

Preferably, however, the optical isolator 38 is used and is an integrated component within the signal encoder 60. Within the optical isolator 38, the input signal activates a light-emitting diode, LED (not shown), which transmits a light signal containing information on the magnitude of the electrical potential to a fiber optic cable. The fiber optic cable, in turn, carries the light signal out of the signal encoder 60 to a photo detector. The photo detector (not shown) converts the light signal containing the magnitude information into an electrical signal.

In a preferred embodiment, the output of the optical isolator 38 is transmitted to a computer I/O interface 40. Contemporary examples of such computer I/O interfaces are Universal Serial Bus, PCMCIA card, PCI card, SCSI and FireWire. The computer I/O interface 40 transmits data between the signal encoder 60 and the data controller 16.

The data controller 16 preferably includes a processor 22 and computer media storage 24. Preferably, the output of the optical isolator 38 is transmitted to a computer I/O interface 40 which transmits digital signals between the collector 14 and the processor 22. The processor 22 uses a software-implemented multiplexer to select the received signals from the computer I/O interface 40. Preferably, the software multiplexer is a program executed by the processor 22 to select given inputs at predetermined times, so that the signal is time-division multiplexed. Thus, the multiplexer 34 selects a corresponding output of the amplifier circuits 32, and then transmits groups of signals in sequence through the analog-to-digital converter 36, the optical isolator 38 and the computer I/O interface 40. The software multiplexer then selects these signals in sequence. For the full set of data from all electrodes 12 in the pattern to be read, the sequences of signals are transmitted to the software multiplexer, whereby each sequence corresponds to the outputs from the electrodes 12. The rate at which the data is stored and sampled is such that no substantial change occurs in the muscle between sample times. Preferably, the data is received and processed in parallel such that sampling rates need not be a consideration in the subsequent analysis. Accordingly, the sEMG measurements from the pattern of electrodes 12 are grouped such that each group has measurements that have been taken at substantially the same time.

Preferably, the collection subsystem data controller 16 further includes a video display 18, a keyboard 20, a graphics program 26, a data reduction program 28, a sound generator 30, and a speaker 31. Via the keyboard 20, a user controls the operation of the data collection subsystem 10 by issuing commands that are processed by the processor to begin and end the receipt and storage of data. The digital electronic activity signals received by the processor 22 are optionally displayed on the video display 18, and stored on the computer media storage 24. The graphic program 26 uses the data received through the processor 22 to preferably generate a graphical display of the variation in electrical signals. The data reduction program 28 preferably compresses data to be stored on the computer media storage 24. The sound generator 30 and speaker 31 enable the output of audio cues to aid an operator of the data collection subsystem 10 to timely instruct a patient regarding the performance of the various motor tasks required by the patient in a preferred method of determining back muscle dysfunction.

The collection subsystem data controller 16 may be a computer like that manufactured by IBM or Apple with a monitor such as, for example, a cathode ray tube (CRT) or liquid crystal display (LCD). A computer executing software is preferably used for the data controller 16 because of the utility and flexibility in programming and modifying the software, displaying results, and running other peripheral applications. Alternatively, the collection subsystem data controller 16 may be implemented using any type of processor or processors that may analyze electrical measurements of muscle activity as described herein. Thus, as used throughout, the term "processor" refers to a wide variety of computational devices or means including, for example, using multiple processors that perform different processing tasks or have the same tasks distributed between processors. The processor(s) may be general purpose CPUs or special purpose processors such as are often conventionally used in digital signal processing systems. Further, multiple processors may be implemented in a server-client or other network configuration, as a pipeline array of processors, etc. Further, some or all of the processing is alternatively implemented with hard-wired circuitry such as an ASIC, FPGA or other logic device. In conjunction with the term "processor," the term "computer media storage" refers to any storage medium that is accessible to a processor that meets the memory storage needs for analyzing electrical measurements of muscle activity.

Figure 1C:
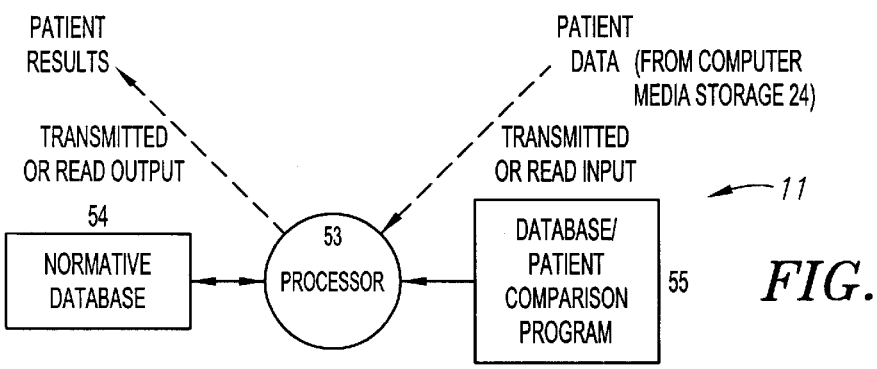
FIG. 1C is an illustration of a preferred embodiment of a data analysis subsystem in the back muscle dysfunction system of the present invention.

FIG. 1C depicts a preferred embodiment of the data analysis subsystem 11 for analyzing the patient data collected and stored by the data collection subsystem 10. The data analysis subsystem 11 preferably comprises a processor 53, a normative database 54 stored on computer media storage, and a database/patient comparison program that is similarly stored in computer media storage and executed by the processor 53. The database processor 53 executing the comparison program 55 is optionally a processor of known design, such a personal computer or a mainframe system, any other form of processor as described in reference to the processor 22, or even the same processor as processor 22, as noted above. In preferred embodiment, the normative database 54 is a database of normal activity and may be one of many such databases in the data analysis subsystem 11 that is used for comparison purposes. Preferably, the normative database 54 contains data regarding a population of individuals whose measurements are considered healthy and which constitute a healthy population of individuals. Additional databases having data from a sufficient number of individuals who have been diagnosed with muscle dysfunction may be established as examined patient databases. Further, sub-databases of the normative database 54 or the examined patient databases according to a variety of classification schemes, may be defined to enable more specific comparison studies with specific patients. Functionally, the data analysis subsystem 11 receives as input patient data from the data collection subsystem 10 and performs a comparative analysis using the normative database 54, and preferably, one or more examined patient databases.

In a preferred embodiment, the database comparison program 55 reads data from the computer media storage 24 and compares the patient's data with the normative database 54 or a sub-database of the normative database 54 to produce a document report addressing the condition of the patient. Data on a patient from the computer media storage 24 is input into the database processor 53. The raw data and calculations from the computer media storage 24 are used by the database comparison program 55 to quantify back muscle dysfunction for a patient. Accordingly, the electrical muscle activity measurements collected for the patient and stored in the computer media storage 24 are used to calculate electrical muscle activity ratio values and other analysis values that are then compared by the database comparison program 55 to the sample values of the normative database 54. Preferably, in quantifying back muscle dysfunction, the processor 53 determines a measure of back muscle dysfunction in response to the comparison of the patient ratios. Preferably, the database comparison program 55 returns a number of conclusions on which a diagnostic evaluation may be based.

Preferably, the conclusions of the database comparison program 55 are based on a comparison of electrical activity measurements. However, the conclusions may additionally be based upon other factors. These other factors include relaxation time and change in relaxation time between activity and rest periods. Another indication of muscle health may be determined by the spectral characteristics of the measured signal. The adipose tissue correction factor is also preferably considered in making the comparison as discussed above.

Figure 2:
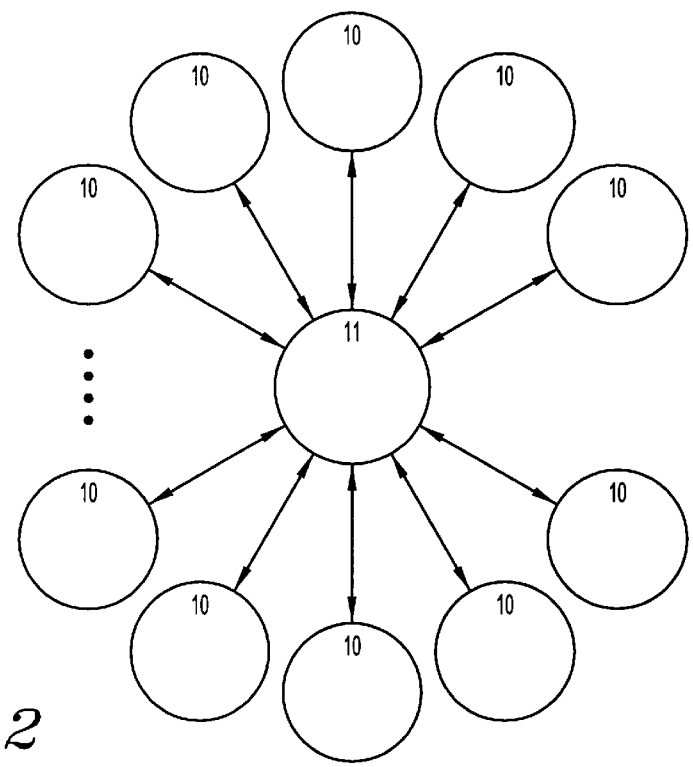
FIG. 2 is an illustration of a preferred embodiment of a communication network implementing a back muscle dysfunction system of the present invention where a data analysis subsystem as depicted in FIG. 1C is networked to a plurality of data collection subsystems as depicted in FIG. 1B.

FIG. 2 illustrates a preferred embodiment of the BMD system 8 implemented as a muscle dysfunction evaluation network where a centralized data analysis subsystem 11 as depicted in FIG. 1C is networked to a plurality of data collection subsystems 10 as depicted in FIG. 1B. FIG. 2 depicts ten data collection subsystems 10 with a single data analysis subsystem 11 purely as an example of a possible network configuration of the BMD system 8. It is understood that a BMD system 8 implemented as a network is not inherently limited in terms of the number of connected subsystems 10, 11. Specifically, in the embodiment shown in FIG. 2, BMD data is collected at one location and analyzed at another location. The data may be provided from one of the data collection subsystems 10 to the data analysis subsystem 11 by any available means. However, the communications for the BMD system 8 are preferably implemented using Internet Communication or switched telephone line services, preferably using 56 Kbps modems or ISDN interfaces. The BMD system 8 is also optionally adapted to high-speed access over available high-speed links, such as T1, T3, ADSL, telephone lines, cable modems or other means of high-speed access. The communications are alternatively implemented using available wireless communicating means, including satellite or terrestrial systems. In an Internet communication configuration, data collection subsystems 10 securely communicate with the data analysis subsystem 8 via an Internet web page that preferably requires login and password entry. Preferably, a mechanism is provided for Internet transmission of collected data from the data collection subsystems 10. Further, an alternative mechanism allows users associated with the data collection subsystems 10 to retrieve analyzed data, preferably in the form of analysis reports. The retrieval process preferably allows the users to have the reports securely downloaded, emailed, faxed or in any other manner transmitted to the data collection subsystem 10, to a fax machine, or to any other data output computer or terminal that can display, produce or otherwise output analysis reports. The retrieval process further allows the reports to be directed using traditional mail.

If the network is wholly implemented in a local area, such as within a clinic or hospital, as a local network such as an intranet, client-server system, or other similarly-sized network, the communications are preferably implemented using systems and protocols that are used for such communications such as Ethernet, TCP/IP, parallel port, serial port, etc. A wireless communication system for communicating the data is optionally implemented, preferably using infrared, RF, one of the ISM (Industrial, Scientific and Medical) bands or other frequencies. In one preferred embodiment, multiple data analysis subsystems in a plurality of local clinics or hospitals communicate with a centralized data analysis subsystem over a wide area network. In this configuration, the databases in the local data analysis subsystems 11 periodically update and are updated by the centralized database subsystem. To the users of the data collection subsystems 10, the network of data analysis subsystems 11 preferably operates as a virtual single analysis subsystem.

Figure 3:
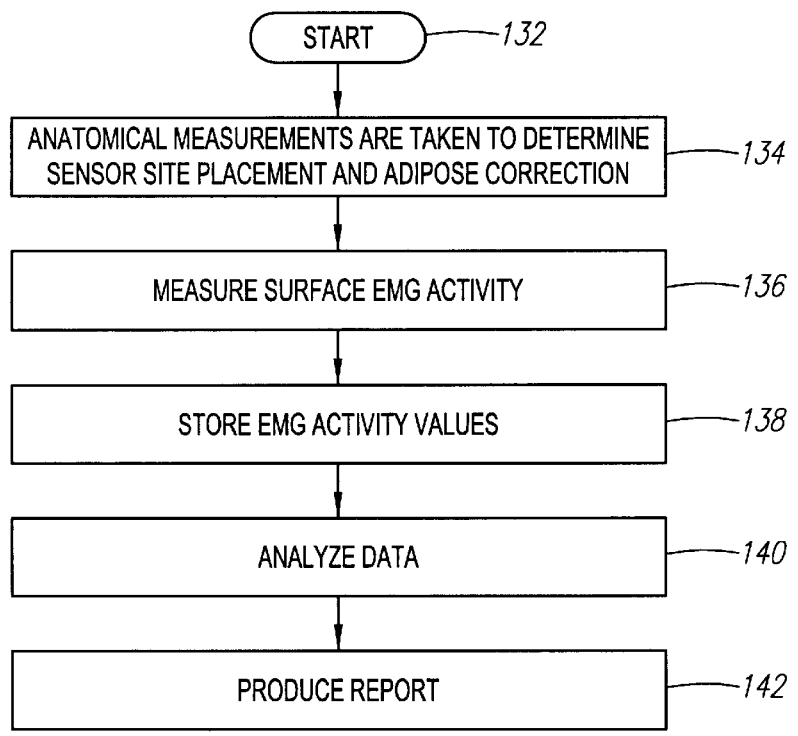
FIG. 3 is a flow chart illustrating basic steps in a preferred method of the present invention for performing back muscle dysfunction analysis.

FIG. 3 illustrates basic steps of a preferred method of determining back muscle dysfunction. In the first step 132, the method for determining back muscle dysfunction is initiated or initialized. The processor 22 initializes the data collection subsystem 10 for data collection. As a second step 134, anatomical measurements are taken to determine sensor site placement and adipose correction. In the next step 136, the electrodes 12 are applied in a pattern across an individual's back and measurements of electrical activity preferably as a set of measurements from the pattern of electrodes are collected. The set of measurements includes a predetermined number of values, corresponding respectively to measurements of electrical activity made at substantially the same time from each of the plurality of electrodes 12 in the pattern.

Figure 4:
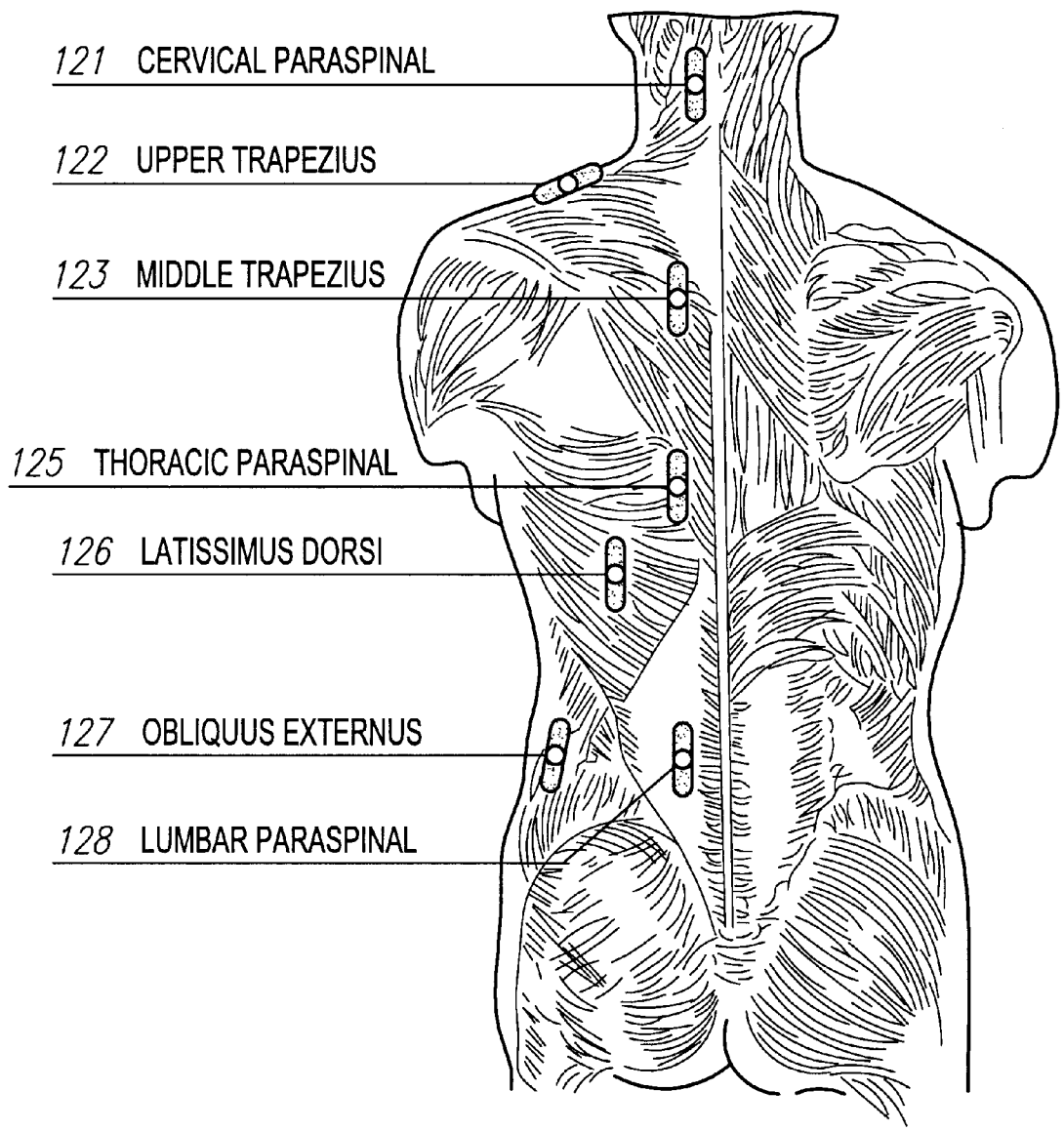
FIG. 4 illustrates the pattern of electrode placements according to a preferred embodiment of the invention.

FIG. 4 is an anatomical diagram of the muscles of the back illustrating the pattern of electrode placements on the back according to the preferred embodiment. Electrodes 12 are illustrated by blackened ovals. The white center-portion in each of the ovals is where the electrode is centered. The electrodes 12 are named in accordance with the corresponding muscles over which they are located. The left side of the pattern of electrodes is illustrated in FIG. 3 and includes a cervical paraspinal electrode 121, an upper trapezius electrode 122, a middle trapezius electrode 123, a thoracic paraspinal electrode 125, a latissimus dorsi electrode 126, an obliquus externus electrode 127, and a lumbar paraspinal electrode 128. A matching number of electrodes are present on the right side in equivalent positions. Thus, preferably fourteen electrodes are placed on the back of the individual or patient whose sEMG signals are being measured. Alternatively, additional or fewer electrodes may be applied to a patient's back, or a completely separate muscle set of muscle sites may be tested.

The electrodes in the preferred embodiment may be applied individually as may be the case with the illustrated electrodes 12 or may, in an alternate embodiment, be mounted in an electrode jacket, not shown. The electrode jacket is worn by the individual and has electrodes similar to the electrodes 12 mounted therein in the desired pattern. The electrodes of the electrode jacket make contact in the appropriate locations when the individual wears the jacket.

Adipose tissue can affect the transmission of electrical activity from the underlying muscle. The adipose tissue attenuates the signal between the underlying muscle and the corresponding electrode on the surface of the skin. A correction factor can be computed for a given adipose tissue thickness that can be applied to every measurement from the corresponding electrode. This correction factor can be derived from regression-based formulas using various anatomical measurements of the patient.

The measurement of electrical activity over a muscle can be indicative of the health of that muscle. More particularly, depending upon how and when the measurement is taken, a significant amount of information may be obtained regarding the health of a muscle. Muscle dysfunction is often indicated by a relatively low electrical output (hypoactivity), a relatively high electrical output (hyperactivity), changes in the electrical output's spectral characteristics, or changes in the output during the relaxation time after activity. With respect to the electrical output's spectral characteristics, if the electrical activity measured at the muscle has frequent variations in amplitude, the signal is said to be a rough signal. This "roughness" in the detected electrical signal is typically an indication of muscle dysfunction.

If a muscle is damaged, the sEMG may indicate muscle substitution. Muscle substitution occurs when another set of muscles is used to compensate for the lack of functionality of the muscle being evaluated, due to the damage to that muscle. Accordingly, muscle substitution can be a measurable indication of damage, as well as an indication of the nature and location of the damage.

In the preferred embodiment, the individual performs a predetermined set of motor tasks during collection of EMG measurements. These motor tasks are carried out via consecutive periods of rest, dynamic muscle engagement, and static muscle engagement. The audio cues from the speaker 31 aid in the instruction of when the patient should begin a motor task, should remain static, or rest. Rest is defined as having the patient stand in a relaxed position with arms at the sides. Dynamic muscle engagement is defined as the process of transitioning from the rest position to the particular static pose required for the specific motor task being performed. Static muscle engagement is defined as having the patient maintain the static pose of the specific motor task for a specific period. As an example, one complete EMG measurement session for a motor task consists of a period of rest, immediately followed by a period of dynamic muscle engagement, with that immediately followed by a period of static muscle engagement. The length of the rest period should equal the combined length of the dynamic and static muscle engagement periods. This sequence of three phases of muscle engagement constitutes one complete EMG measurement session. This one complete EMG measurement session is itself repeated several times for each motor task in the process of completing acquisition of EMG data sufficient for analysis by the data analysis subsystem 11.

In the preferred embodiment, only the EMG data collected during the periods of static muscle engagement are used. In an alternate embodiment, EMG data collected during the rest and dynamic periods as well as the static period are used in the data analysis conducted.

Electrical activity measurements are made at specific periods within the movements. Preferably, measurements are made during the range of motion and at the endpoints of the motion. This dynamic measurement of muscles during a motor task and the measurement of muscles under tension give a more accurate picture of the muscle action. Relaxed measurements are subject to small postural variations that are hard to correct.

Figure 5:
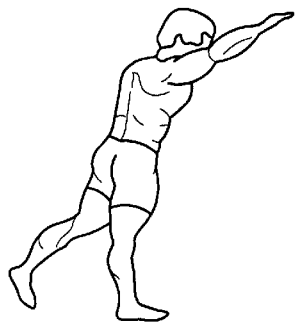
FIGS. 5–13 illustrate motions performed in accordance with a preferred embodiment of the present invention.
Figure 6:
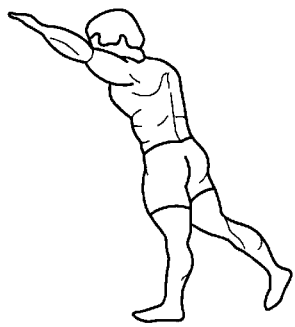
Figure 7:
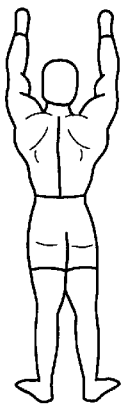
Figure 8:
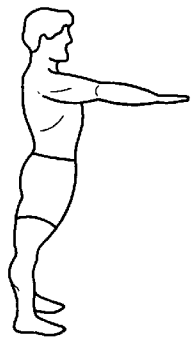
Figure 9:
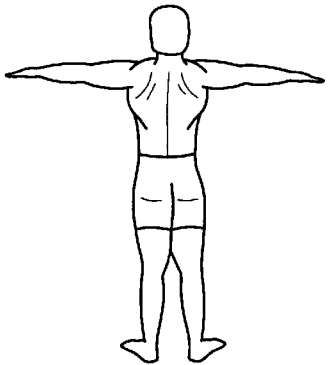
Figure 10:
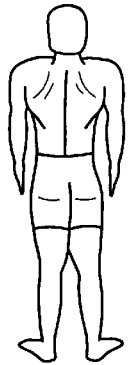
Figure 11:
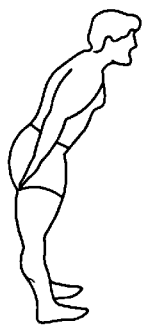
Figure 12:
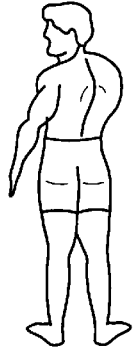
Figure 13:
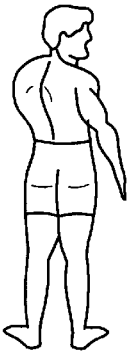

FIGS. 5–13 illustrate the movements used during the dynamic measurements. FIG. 5 illustrates the right arm overhead movement, whereby the individual extends the right arm overhead, and the left leg backward. FIG. 6 illustrates the left arm overhead movement, whereby the individual extends the left arm overhead, and the right leg backward. FIG. 7 illustrates the arms overhead movement, whereby the individual extends both arms overhead. FIG. 8 illustrates the forward arm flexion movement, whereby the individual extends both arms forward to a 90-degree angle from the body, with the palms facing downward. FIG. 9 illustrates the arm abduction movement, whereby the individual extends both arms from the sides to a 90-degree angle from the body, with the palms of the hand facing down. FIG. 10 illustrates the shoulder shrug movement, whereby the individual shrugs both shoulders upward. FIG. 11 illustrates the forward bow movement, whereby the individual bows 45-degrees forward at the waist, with both arms to the sides. FIG. 12 illustrates the left trunk rotation movement, whereby the individual rotates to the left with a maximum range of motion at the hips and head. FIG. 13 illustrates the right trunk rotation movement, whereby the individual rotates to the right with a maximum range of motion at the hips and head.

In a preferred embodiment, there are 7.2-second motion periods and 7.2-second rest periods, and the full pattern of the electrodes 12 is sampled about 2000 times per second. As a next step 138 in the preferred method, these measurements are stored in the processor 22 in computer media storage 24 in the manner described above. Alternatively, other sampling rates and groups of measurements are used.

The computer media storage 24 preferably only contains raw EMG activity data. However, the preferred embodiment ultimately employs ratios of EMG activity data in its analysis. This ratio technique eliminates much of the variability inherent in using sEMG to measure muscle activity.

In accordance with a preferred embodiment, the next step 140 is to analyze the data using a previously compiled database of sets of measurements from a plurality of individuals by making diagnostic comparisons of data. In the previously performed process of compiling the database of measurements, electrical muscle activity measurements for asymptomatic individuals are collected in a number sufficient to develop a sample representative of a population. Preferably, a group of individuals is selected for collection of electrical muscle activity measurements. The individuals can be considered a normative set of individuals to which patients can be compared.

In a final basic step 142 of the preferred method of analyzing for muscle dysfunction, the diagnostic conclusions generated by the data comparison program 55 are output in a document report 58. The document report 58 preferably provides patient identifying data and reports diagnostic conclusions and helps determine a desirable therapeutic treatment.

In preferred embodiment of the system and method of analyzing back muscle dysfunction, the data analysis step 140 depicted in FIG. 3 is performed as a series of substeps described below and illustrated in FIGS. 14 and 15A–C. Preferably, the data for patient analysis and the compilation of the normative database 54 are concerned primarily with the periods in which the patients are statically engaged in motor tasks. First, a sub-step 146 of averaging the data collected during each respective motor task is performed. Thus, the sample measurements taken during the periods of static engagement for a particular muscle and a particular motor task are averaged.

In the next sub-step 148, the averaged electrical activity data measurements for each muscle are adjusted for the adipose thickness underlying the corresponding electrode. The correction factor to the averaged measurements is preferably computed by processor 53 using regression-based formulas to determine "true" EMG values for each muscle based on the EMG measurements made at the skin's surface. In one preferred embodiment, the attenuation of the EMG signals due to adipose thickness are accounted for according to the equation:

$$EMG \approx sEMG * antilog(B * Adipose)$$

where EMG is a regression-based estimate of the EMG at a muscle, sEMG is the EMG measured at the skin's surface, Adipose is a factor relating to the adipose thickness underlying the electrode, and B is a regression coefficient that has one of two values depending on the gender of the patient. Notice that as Adipose approaches zero, sEMG approaches EMG. Alternatively, other relationships between Adipose, sEMG, and EMG are used. For example, in one alternative embodiment, an inverse relationship is used:

$$EMG = Adipose * sEMG/B.$$

In another alternative embodiment, an inverse square relationship is applied to determine the estimated EMG at the muscle:

$$EMG = Adipose^2 * sEMG/B.$$

Ideally, to determine the Adipose values that are inserted into one of the above adipose attenuation formulas, the adipose thickness measurements for each patient at each muscle are measured directly. These measurements may be obtained via caliper measurements of the skin fold or by using ultrasound. Ultrasound devices potentially provide the most precise adipose measurements. Preferably, the ultrasound device for performing such measurements is designed to be inexpensive and easy to use such that patient measurements of adipose are practical. Further, the ultrasound device has post-processing to provide as output actual adipose measurements rather than requiring medical personnel to subjectively estimate adipose thickness from an ultrasound image.

In an alternative preferred embodiment, rather than requiring medical personnel to make adipose measurements for each tested patient, regression-based formulas are used to estimate the adipose correction factors. In one embodiment, the regression formula has the following form:

$$Adipose_i = B_0 + B_1 * Height_i + B_2 * Weight_i \quad (1).$$

In equation (1) above, Adipose is the adipose correction factor, Height is the height of the patient in specified units, Weight in the weight of the patient in specified units, and (i) is a patient or observation number index. $B_0$, $B_1$, and $B_2$ are regression coefficients that vary depending on gender and the bilateral muscle group at which an adipose value is desired. $B_0$ preferably is a coefficient relating specifically to gender, $B_1$, is a coefficient relating to height, and $B_2$ is a coefficient relating to weight. Given preferably seven examined bilateral muscle groups and two genders, preferably 14 sets of coefficients are established to enable the regression-based adipose thickness estimation. By using such a formula, only efficiently measured anatomical measurements for each patient need be determined in the field, rather direct measurements of adipose that require more time and/or complex measurement devices.

In another regression-based embodiment, the following more generic formula is used:

$$Adipose_i = B_0 + B_1 X_{1i} + \ldots + B_n X_{ni} \quad (2).$$

In equation (2) above, $X_{1i}, X_{2i} \ldots X_{ni}$ are measurement values such as Height and Weight that were specified in equation (1). However, equation (2) enables other types of anatomical measurements to factor into the determination of Adipose, up to (n) types. Such other types of measurements may include, but are not limited to Body Mass Index (BMI), body type, such as muscular, obese and slim, waist circumference, chest circumference, wrist circumference, and light transmissiveness of skin/adipose tissue. In equation (2) as in equation (1), $B_0, B_1, \ldots B_n$ are previously established adipose thickness coefficients that relate to the types of measurements they modify.

To obtain meaningful values for the adipose thickness coefficients, adipose measurement tests on a large sample of patients are preferably performed. In performing such tests for developing the regression-based formulas, the ultrasound or other measurement devices that enable precise measurements of adipose may be used. Regressions are then performed to account for the interaction effects of the various types of anatomical measurement, and to finally determine sets of B coefficient values.

Figure 14:
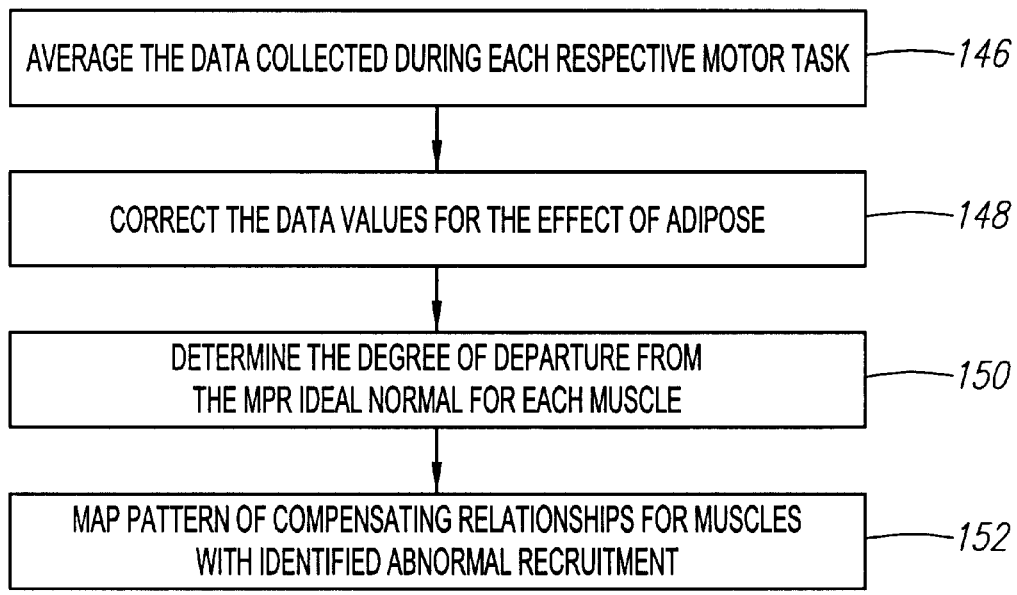
FIG. 14 is a flow chart detailing preferred sub-steps for performing the data analysis step depicted in FIG. 3.

Returning to the sub-steps of the data analysis illustrated in FIG. 14, in the next sub-step 150, the degree of departure from an ideal normal condition or level of dysfunction for each muscle is determined. The ideal normal condition represents a specific state or condition within a normal condition range. The identification and level of the dysfunctional muscles of sub-step 150 is determined by a procedure involving comparing patient ratio data to sample ratio data stored in a sample database, i.e. a normative database. In effect, the procedure is a muscle pattern recognition (MPR™) procedure in which a sample set of muscular responses are compared to a library database of such responses to determine identifying characteristics of the sample set. The steps depicted in FIGS. 15A–C illustrate the procedure of sub-step 150.

Figure 15A:
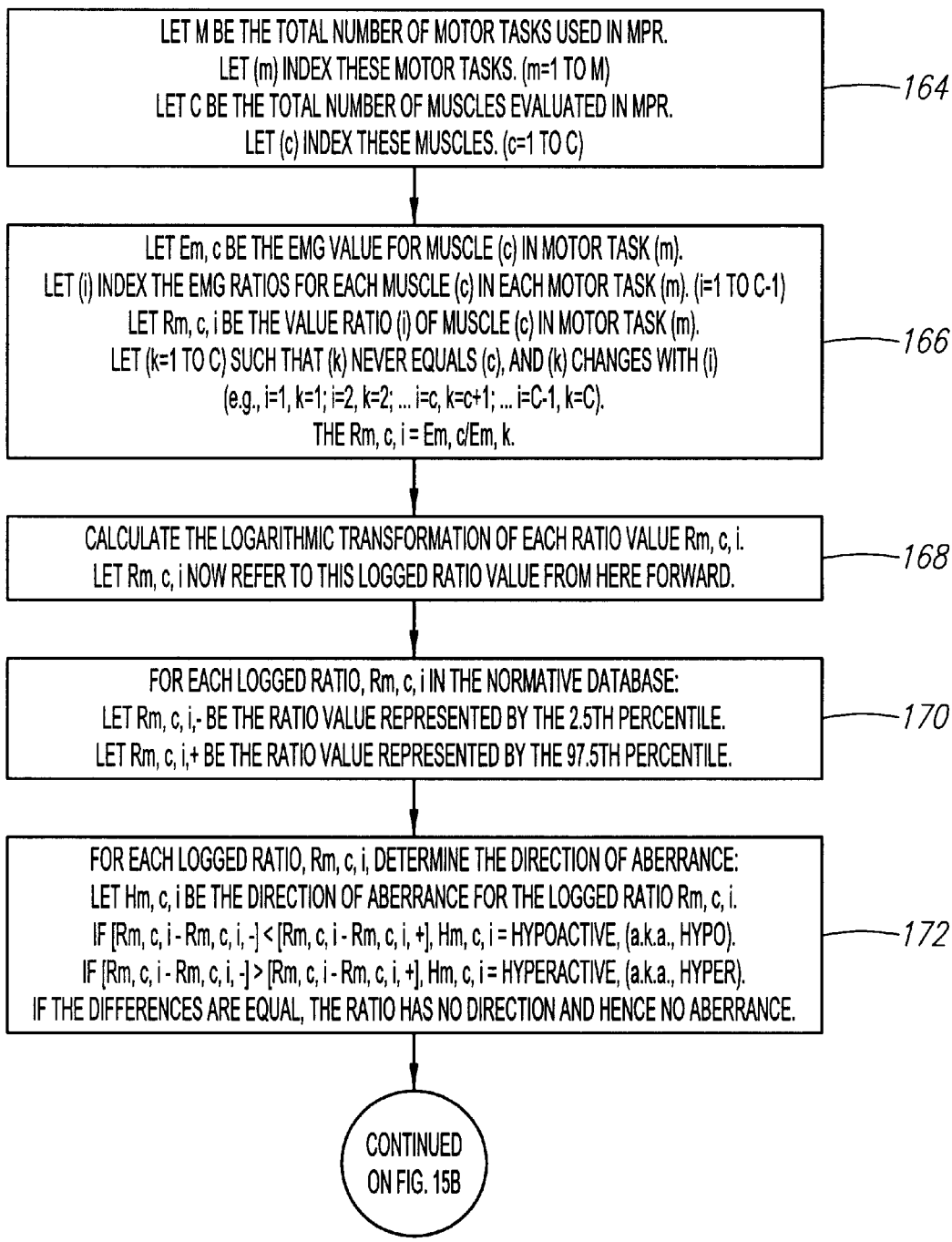
FIGS. 15A–15C depict a flow chart detailing preferred sub-steps for the step of FIG. 14 of determining a muscle's degree of departure from an ideal normal condition.
Figure 15B:
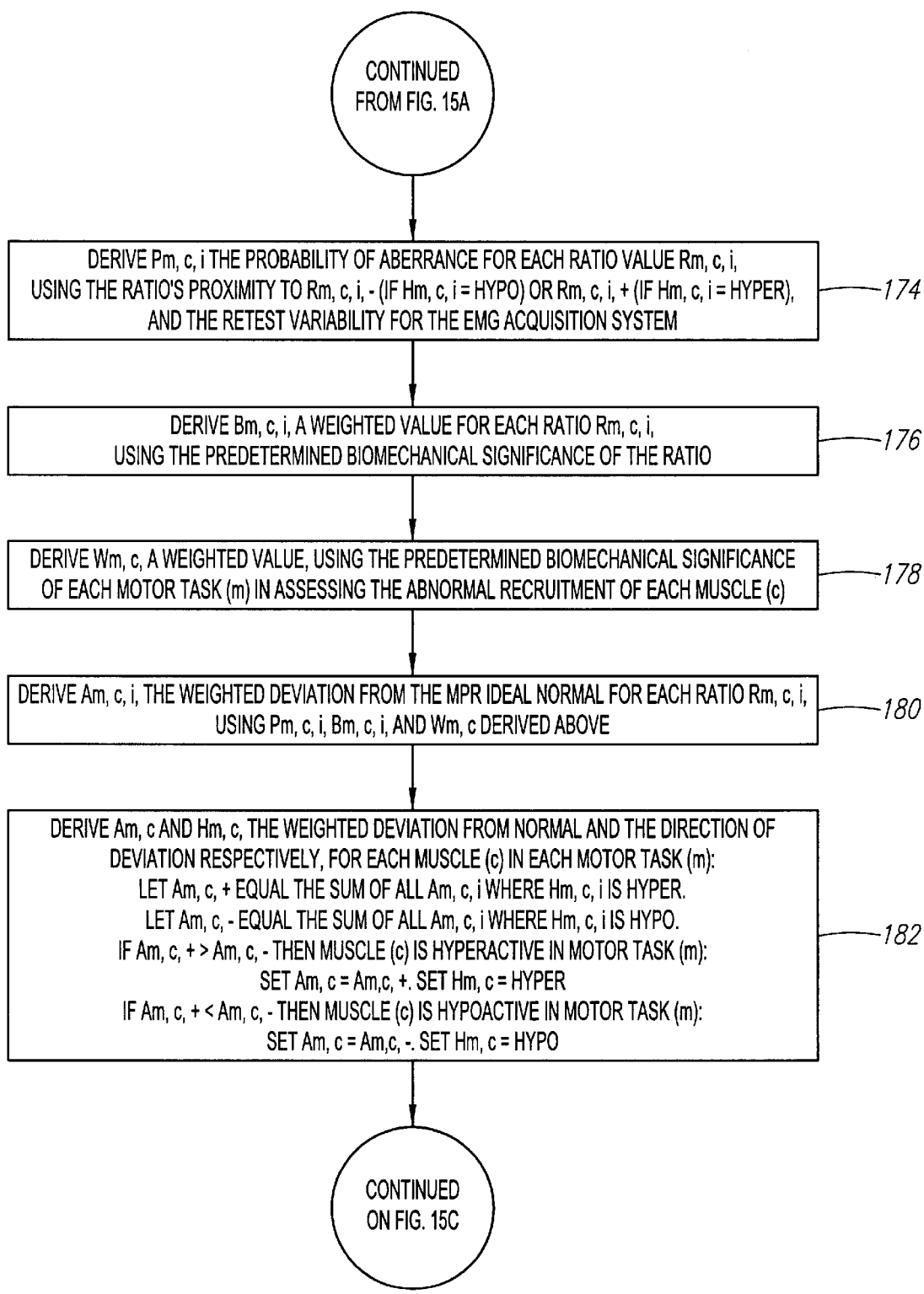
Figure 15C:
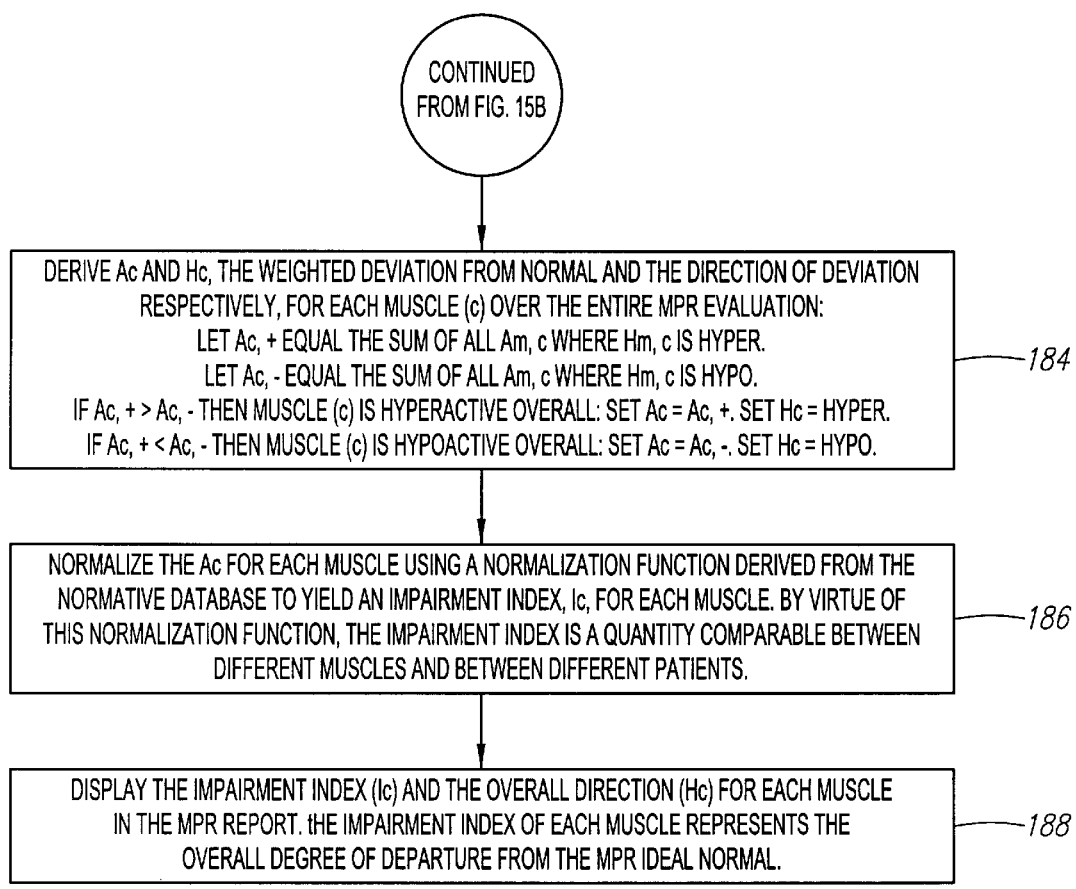

Referring now to FIGS. 15A–C, the MPR™ analysis for determining dysfunctional muscles as represented in sub-step 150 of FIG. 14 comprises the following steps. In the first step 164, the total number of motor tasks (M) to be used in the MPR™ analysis and the total number of muscles (c) to be evaluated are identified. Each combination of motor tasks and muscles are kept track of individually. In the next step 166, for each combination of muscle and motor task, a set of EMG measurements $E_{m,c}$ are established. From these measurements, each step of the MPR™ analysis preferably generates one or more types of values that are termed herein generally as "analysis values." Specifically, in initiating the MPR™ analysis, an index (i) to ratio values, R, of EMG measurements within each motor task is established. Thus, $R_{m,c,i}$ is the ratio value between the EMG measurement for muscle (c) in motor task (m), $E_{m,c}$, and the EMG measurement for muscle (i) in motor task (m), $E_{m,i}$. To assure meaningful ratio values, (i) never equals (c). In the next step 168, a logarithmic transformation of each of the previously calculated EMG ratio values, $R_{m,c,i}$, is determined.

In the next step 170, with the EMG ratio values, $R_{m,c,i}$, now being logarithmic, for each type of ratio $R_{m,c,i}$ in the normative data base 54, two predetermined ratio thresholds are now used. For each type of ratio $R_{m,c,i}$, the first ratio threshold, $R_{m,c,i,-}$, is between the minimum ratio and the median ratio in the normative database. The second ratio threshold, $R_{m,c,i,+}$, is between the median ratio and the maximum ratio in the normative database. Preferably, $R_{m,c,i,-}$ is set at the $2.5^{th}$ percentile level value in the range of values for $R_{m,c,i}$ in the normative database and $R_{m,c,i,+}$ is set at the $97.5^{th}$ percentile level value. These thresholds guarantee a window of ratios that comprise 95% of the normative database. By thresholding in this manner, the analysis is independent of any assumptions regarding the distribution of the normative database 54. Thus, in the next step 172, a direction of aberrance, $H_{m,c,i}$ for each muscle pair, (c) to (i), for each motor task (m) is determined based on the value of the logged ratio $R_{m,c,i}$ in relation to its corresponding ratio thresholds, $R_{m,c,i,-}$ and $R_{m,c,i,+}$. In particular, if $$|R_{m,c,i}-R_{m,c,i,-}|<|R_{m,c,i}-R_{m,c,i,+}|,$$

then $H_{m,c,i}$ equals Hypoactive (HYPO). Alternatively, if $$|R_{m,c,i}-R_{m,c,i,-}|>|R_{m,c,i}-R_{m,c,i,+}|,$$

then $H_{m,c,i}$ equals Hyperactive (HYPER). Finally, if the absolute values of the differences are equal, then $H_{m,c,i}$ is zero, as there is no direction of aberrance.

In the next step 174, a probability of aberrance, $P_{m,c,i}$, for each logged ratio value, $R_{m,c,i}$, is determined. The probability of aberrance, $P_{m,c,i}$, is a probability measure that combines the actual aberrance of each ratio value, $R_{m,c,i}$, based on its proximity from $R_{m,c,i,-}$ and $R_{m,c,i,+}$ and the EMG measurement system's retest variability. Knowledge of retest variability is required to estimate the inherent variability introduced by the MPR™ analysis as a whole. Statistics estimating the variability of the MPR™ analysis in recording each ratio under the conditions of retest are preferably previously computed from a gathered retest data set. Using the known normative distribution and the retest variability model, the probability of aberrance value, $P_{m,c,i}$, is computed for each ratio value by first determining the estimated standard deviation of the ratio, s, as determined by the retest variability model. Then, a value for a Line of Aberrance (LOA) is defined as either $R_{m,c,i,-}$ or $R_{m,c,i,+}$ depending upon the ratio's direction of aberrance. Specifically, If $H_{m,c,i}$=HYPO: LOA=$R_{m,c,i,-}$, If $H_{m,c,i}$=HYPER: LOA=$R_{m,c,i,+}$.

Then, a z-score, z, of the LOA relative to the ratio's modeled variability is determined and is preferably given by:

$z$=(LOA−$R_{m,c,i}$)/s.

Then, the probability of aberrance, $P_{m,c,i}$, for the ratio is preferably given by the following formulas:

If $H_{m,c,i}$=HYPO: $P_{m,c,i}$=OTCDF(z),

If $H_{m,c,i}$=HYPER: $P_{m,c,i}$=1−OTCDF(z),

If $H_{m,c,i} \neq$HYPO and $H_{m,c,i} \neq$HYPER: $P_{m,c,i}$=0.

In the above equations, OTCDF(z) is the One-Tailed Cumulative Distribution Function for the standard normal distribution; i.e., OTCDF(z) is the probability that a standard normal random variable is less than z. For example,

OTCDF(1.96)=0.975.

Thus, the probability of aberrance, $P_{m,c,i}$, is the probability of the patient's ratio exceeding its LOA. Further, by example, the probability of aberrance where $H_{m,c,i}$ is neither HYPO nor HYPER is exactly zero, and the probability of aberrance where $R_{m,c,i}$ is equal to the LOA is exactly 50%.

In the next step 176, a weighted value, $B_{m,c,i}$, for each logged ratio value, $R_{m,c,i}$, is derived. The values for $B_{m,c,i}$ are weights assigned to each ratio value in each motor task based upon the relative biomechanical significance of the muscle relationship reflected by the muscles involved in the ratio during the specific motor task. These weighted values are predetermined portions of the MPR™ analysis, arrived at empirically using principles of biomechanics.

In the next step 178, another weighted value, $W_{m,c}$, is determined using the predetermined bio-mechanical significance of each motor task (m) in assessing abnormal recruitment of each muscle (c). The values for $W_{m,c}$ are weights assigned to each motor task for each muscle. These weighted values are based upon the predictive value of the specified motor task in assessing performance of the specified muscle. The weighted values are predetermined portions of the MPR T analysis, arrived at empirically using principles of biomechanics. Then, in the next step 180, using the weighted values derived in the previous three steps, a weighted deviation value from the ideal normal, $A_{m,c,i}$, for each logged ratio value, $R_{m,c,i}$, is determined. The value for $A_{m,c,i}$ for each ratio value is preferably simply the product of the three weighted values determined above. That is, $$A_{m,c,i} = P_{m,c,i} * B_{m,c,i} * W_{m,c}.$$

In the next step 182, an overall deviation from normal, Amc, and a direction of deviation from normal, $H_{m,c}$, for each muscle (c) in each motor task (m) is determined. These measures characterize the performance of each muscle in a given motor task in a manner that is independent of each muscle's relationship to other muscles in performing the given motor task. Preferably, in determining values for $A_{m,c}$ and $H_{m,c}$, a hyperactive weighted deviation value, $A_{m,c,+}$, is determined by summing all values for $A_{m,c,i}$ for which $H_{m,c,i}$ has a value of HYPER. Then, a hypoactive weighted deviation value, $A_{m,c,-}$, is determined by summing all values for $A_{m,c,i}$ for which $H_{m,c,i}$ has a value of HYPO. If $A_{m,c,+} > A_{m,c,-}$, then muscle (c) is considered hyperactive in motor task (m). In this case, $A_{m,c}$ is set equal to $A_{m,c,+}$ and $H_{m,c}$ equals HYPER. Alternatively, if $A_{m,c,+} < A_{m,c,-}$, then muscle (c) is considered hypoactive in motor task (m). In this case, $A_{m,c}$ is set equal to $A_{m,c,-}$ and $H_{m,c}$ equals HYPO.

In step 184, the procedure continues forward by eliminating the particular motor task as a variable in the characterization of each muscle and, instead, characterizing each muscle's state independent of the motor task performed. In step 184, values for the weighted deviation from normal, $A_c$, and the direction of deviation from normal, $H_c$, are determined for each muscle. Preferably, in a manner similar to the calculation performed above, in determining values for $A_c$ and $H_c$, a hyperactive muscle deviation value, $A_{c,+}$, is determined by summing all values for $A_{m,c}$ for which $H_{m,c}$ has a value of HYPER. Then, a hypoactive muscle deviation value, $A_{c,-}$ is determined by summing all values for $A_{m,c}$ for which $H_{m,c}$ has a value of HYPO. If $A_{c,+} > A_{c,-}$, then muscle (c) is considered hyperactive overall. In this case, $A_c$ is set equal to $A_{c,+}$ and $H_c$ equals HYPER. Alternatively, if $A_{c,+} < A_{c,-}$, then muscle (c) is considered hypoactive overall. In this case, $A_c$ is set equal to $A_{c,-}$ and $H_c$ equals HYPO.

In step 186, the values for $A_c$ are normalized using a normalization function based on the statistics compiled from the normative database to determine an Impairment Index™, $I_c$, for each muscle. $I_c$ thereby represents a scale that allows for immediate recognition of the level of impairment of a muscle, regardless of the type of muscle or the patient involved. Specifically, in order to establish the extent of dysfunction within each muscle, a common frame of reference for muscle-to-muscle comparison is required. To realize this, each $A_c$ value is normalized by a muscle-specific function derived from the normative database. These muscle-specific normalization functions are preferably derived as follows.

First, $A_c$ values are computed for every muscle for all subjects, N, within the normative database. Then, the distribution of each muscle's $A_c$ value within the normative database is examined. Specifically, certain percentiles of the $A_c$ values in the normative database population are determined for each muscle. In the preferred embodiment, these percentile values are determined at intervals of five, from five to 90, with the $1^{st}$ percentile also determined (i.e., the $1^{st}$, $5^{th}$, $10^{th}$, $15^{th}$, $20^{th}$, ..., $80^{th}$ $85^{th}$, and $90^{th}$ percentiles). After the $90^{th}$ percentile, percentiles from 90 to 99 are preferably determined at intervals of length 1 (i.e., $90^{th}$, $91^{st}$, $92^{nd}$, ..., $98^{th}$, and $99^{th}$). The $99^{th}$ percentile is then preferably established as a so-called normative cutoff value or abnormal cutoff value, which defines a separation point between "normal" and "abnormal." That is, all $A_c$ values below the cutoff are considered normal, and all above are abnormal. Thus, given a particular muscle, for 1% of the normative database, that muscle is abnormal (i.e., a predetermined false positive rate).

Piece-wise linear interpolation functions (interpolants) are then constructed using standard mathematical techniques, where the normative database percentiles are used as the node points of each interpolant function. The idea of the interpolant function is to "map" the often-different $A_c$ values for each muscle to the same basic function. A different interpolant function may be prepared for each muscle. The interpolant functions are preferably linear, although higher order interpolant functions such as quadratic functions are alternatively used. Before this mapping, all the $A_c$ values are in "different units of measure" and are incomparable. After the mapping has converted the $A_c$ values to an Impairment Index™ for each muscle, the muscles are effectively measured in the "same units" and comparable to one another.

The interpolant function for each muscle is preferably determined by first establishing the $1^{st}$, $5^{th}$, $10^{th}$, ..., $85^{th}$, $90^{th}$, $91^{st}$, $92^{nd}$, ..., $98^{th}$, and $99^{th}$ normative database percentiles for the $A_c$ values. The finally determined Impairment Index™ is preferably approximately linear with respect to percentile. For example, the $99^{th}$ percentile may be required to map to a specific value in the Impairment Index™ that would always indicate a threshold for an abnormal muscle. In the preferred embodiment, this specific value is labeled the "Index of the Abnormal Cutoff" (IAC).

From there, the Impairment Index™, $I_c$, corresponding to any of the other percentiles preferably is a value that is a fraction of the IAC value. The fraction preferably equals the percentile's fraction of the $99^{th}$ percentile. Thus, where $A_c(p)$ is the $p^{th}$ normative percentile of the $A_c$ values, the Impairment Index™, $I_c$, for the $p^{th}$ percentile is given by:

$$I_c(A_c(p)) = IAC * A_c(p) / A_c(99^{th})$$

with p being each of the percentiles listed above.

The unique piece-wise linear interpolant function is created using standard mathematical techniques. The interpolant function is such that the values of $A_c$ at each of the node point percentiles are mapped by the interpolant function to their corresponding Impairment Indexes™. The scheme guarantees that the dysfunction of different muscles in different subjects can be meaningfully compared using the Impairment Index™. To determine an interpolant function segment, $S_i$, values, $x_i$, are defined to be equal to normative database values of $A_c$ for the specific percentiles listed above, where (i) is the number of segments from 1 to n. Thus, $$x_1=A_c(1^{st}), x_2=A_c(5^{th}), \ldots, x_{n-1}=A_c(98^{th}), \text{ and } x_n=A_c(99^{th}).$$

Also, $y_i$ is defined to be $I_c(x_i)$, noting that $y_n$=IAC. Further, $x_0$ and $y_0$ are preferably set to equal to zero. The interpolant function segment, $S_i$, is then defined to be the line segment with the endpoints $(x_{i-1}, y_{i-1})$ and $(x_i, y_i)$, for i=1 to n. The general equation, therefore, for each segment $S_i$ is given by:

$$S_i(x) = y_i + (x-x_i)*(y_i-y_{i-1})/(x_i-x_{i-1}), \text{ with } x_{i-1} \leq x \leq x_i$$

in which $$I_c(A_c) = S_i(A_c), \text{ for } 0 \leq x_{i-1} \leq A_c \leq x_i \leq x_n.$$

The entire piece-wise linear interpolant is identical to the (n) line segments $S_l$ to $S_n$.

For values of $A_c$ above the $99^{th}$ normative database percentile, a linear extrapolation function is determined. The extrapolant function maps the value of $A_c$ to the line continued from the segment between zero and the $99^{th}$ percentile. The ordinate on this line corresponding to the abscissa represented by $A_c$ becomes the Impairment Index™. The equation for the extrapolant function, $S_{ext}(x)$, is given by:

$$S_{ext}(x) = x*y_n/x_n, \text{ with } x \geq x_n,$$

in which $$I_c(A_c) = S_{ext}(A_c), \text{ for } A_c > x_n.$$

Through the procedure described above, a separate normalization function is created for each muscle group examined through the muscle dysfunction analysis system 10.

In step 188, the Impairment Index™, $I_c$, for each muscle representing the overall degree of departure from normal and the overall direction of deviation, $H_c$, for each muscle are displayed, recorded and/or otherwise provided in a report.

Figure 16:
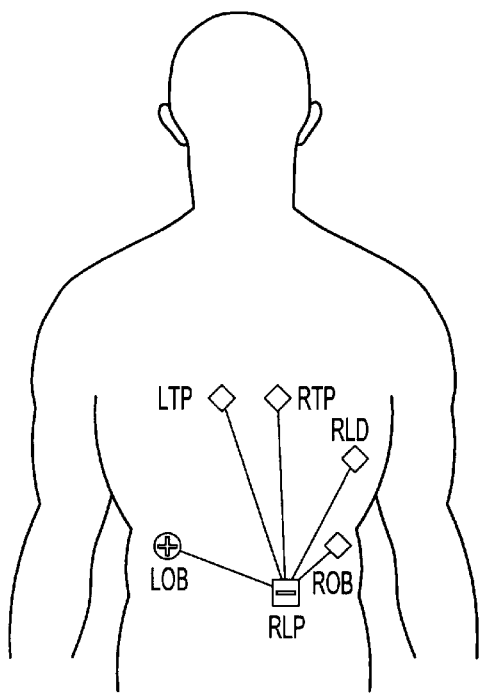
FIG. 16 is a diagram of an exemplary evaluation report for a patient experiencing back muscle dysfunction.

After the determination of the dysfunctional muscles, as illustrated in FIGS. 15A–C, as a final sub-step 152 of the analysis procedure shown in FIG. 14, the patterns of compensating relationships for dysfunctional muscles are mapped. These patterns are based on the muscle activity levels and the kinesiological relationships of the muscles. The mapped patterns graphically illustrate the muscle dysfunction and assist the physician in selecting an appropriate course of therapy. An illustrative example of a mapped pattern of dysfunction is shown in FIG. 16.

It will be apparent to those skilled in the art that various modifications, variations and additions can be made in the method for determining back muscle dysfunction of the present invention without departing from the scope or spirit of the invention. Thus, it is intended that the present invention cover the modifications, variations and additions provided that they come within the scope of the appended claims and their equivalents.

What is claimed is:

1. A method for determining muscle dysfunction of a subject, the method comprising the steps of:
    (a) selecting a plurality of sites on the subject for sensing muscle electrical activity;
    (b) calculating adipose thickness factors for the plurality of sites;
    (c) making electrical activity measurements for the plurality of sites;
    (d) analyzing the electrical activity measurements and determining thereby analysis values for a plurality of muscles, each of the plurality of muscles corresponding to a respective one of the plurality of sites, and in determining the analysis values, factoring the adipose thickness factors into the electrical activity measurements;
        the adipose thickness factors being determined by applying results of obtained measurements from a sampling of individuals, the results relating adipose thickness to general characteristics measured for the individuals, at least one general characteristic of the subject corresponding to at least one of the general characteristics measured for the individuals;
        the results being represented in a set of coefficients that are applied to a formula, each coefficient relating to one of the at least one general characteristic of the subject and to one site of the plurality of sites on the subject.

2. The method of claim 1, the formula having a form:

$$\text{Adipose} = B_0 + B_1X_1 + \ldots + B_nX_n,$$

wherein $B_0$ through $B_n$ comprise the set of coefficients for a given site, $X_1$ through $X_n$ represent values for a different one of the at least one general characteristic of the subject, and n represents the number of the at least one general characteristic.

3. The method of claim 1, wherein the coefficients are regression-based coefficients.

4. The method of claim 1, the at least one general characteristic of the subject being a gender, a height, a weight, a Body Mass Index, a body type, a waist circumference, a chest circumference, a wrist circumference, or a light transmissiveness of skin.

5. A method for determining muscle dysfunction of a subject, the method comprising the steps of:
    (a) selecting a plurality of sites on the subject for sensing muscle electrical activity;
    (b) calculating adipose thickness factors for the plurality of sites;
    (c) making electrical activity measurements for the plurality of sites;
    (d) analyzing the electrical activity measurements and determining thereby analysis values for a plurality of muscles, each of the plurality of muscles corresponding to a respective one of the plurality of sites, and in determining the analysis values, factoring the adipose thickness factors into the electrical activity measurements;
        the adipose thickness factors being determined by applying a formula that includes a set of coefficients, each coefficient relating to one of the plurality of sites on the subject.

6. A method for determining muscle dysfunction of a subject, the method comprising the steps of:
    (a) selecting a plurality of sites on the subject for sensing muscle electrical activity;
    (b) making electrical activity measurements for the plurality of sites; and
    (c) performing an analysis of the electrical activity measurements, the analysis comprising steps of determining from the electrical activity measurements analysis values for each of a plurality of muscles and determining from the analysis values a degree of departure from a normal condition, wherein the degree of departure for the analysis values is normalized with respect to the plurality of muscles, wherein the normal condition is an ideal normal condition.

7. A method for determining muscle dysfunction of a subject, the method comprising the steps of:
   (a) selecting a plurality of sites on the subject for sensing muscle electrical activity;
   (b) making electrical activity measurements for the plurality of sites; and
   (c) performing an analysis of the electrical activity measurements, the analysis comprising steps of determining from the electrical activity measurements analysis values for each of a plurality of muscles and determining from the analysis values a degree of departure from a normal condition, wherein the degree of departure for the analysis values is normalized with respect to the plurality of muscles;
   the step of making the electrical activity measurements at a plurality of sites being performed during specific periods in the execution of a set of motor tasks, and the degree of departure being determined by selectively integrating the analysis values across the set of motor tasks.

8. A method for determining muscle dysfunction of a subject, the method comprising the steps of:
   (a) selecting a plurality of sites on the subject for sensing muscle electrical activity;
   (b) making electrical activity measurements for the plurality of sites; and
   (c) performing an analysis of the electrical activity measurements, the analysis comprising steps of determining from the electrical activity measurements analysis values for each of a plurality of muscles and determining from the analysis values a degree of departure from a normal condition, wherein the degree of departure for the analysis values is normalized with respect to the plurality of muscles;
   the electrical activity measurements relating to a performance of a motor task, and the analysis further comprising a step of determining a set of relationships for each of the analysis values, each relationship in the set for an analysis value relating the analysis value to one of the other analysis values as a pair, and the degree of departure being determined by selectively integrating across the set of relationships.

9. The method of claim 8, each relationship including a weighting factor that reflects a biomechanical significance in the execution of a motor task correlating the muscles associated with the pair of analysis values.

10. The method of claim 8, each relationship including a weighting factor that reflects a biomechanical significance that correlates the motor task with the one of the plurality of muscles associated with the analysis value.

11. The method of claim 8, each relationship including a factor that reflects a systematic variability in measurement of electrical activity.

12. A system for determining muscle dysfunction of a subject, the system comprising:
   (a) a plurality of electrical activity sensors for measuring electrical activity at a respective plurality of sites on the subject; and
   (b) a processor for determining adipose thickness factors based on at least one general characteristic of the subject for the plurality of sites on the subject, and for analyzing the electrical activity and determining therefrom analysis values for a plurality of muscles, each of the plurality of muscles corresponding to a respective one of the plurality of sites, wherein determining analysis values comprises factoring the adipose thickness factors into the measured electrical activity, the processor determining the adipose thickness factors by applying results of obtained measurements from a sampling of individuals, the results relating adipose thickness to general characteristics measured for the individuals, the at least one general characteristic of the subject corresponding to at least one of the general characteristics measured for the individuals.

13. The system of claim 12, the processor determining the adipose thickness factors by representing the results in a set of coefficients that are applied to a formula, each coefficient relating to one of the at least one general characteristic of the subject and to one site of the plurality of sites on the subject.

14. The system of claim 13, the formula having a form:

$$\text{Adipose} = B_0 + B_1 X_1 + \ldots + B_n X_n,$$

wherein $B_0$ through $B_n$ comprise the set of coefficients for a given site, $X_1$ through $X_n$ comprise values for a different one of the at least one general characteristic of the subject, and n is the number of the at least one general characteristic.

15. The system of claim 13, wherein the coefficients are regression-based coefficients.

16. The system of claim 13, the at least one general characteristic of the subject being a gender, a height, a weight, a Body Mass Index, a body type, a waist circumference, a chest circumference, a wrist circumference, or a light transmissiveness of skill.

17. A system for determining muscle dysfunction of a subject, the system comprising:
   (a) a plurality of electrical activity sensors for measuring electrical activity at a respective plurality of sites on the subject; and
   (b) a processor for determining adipose thickness factors based on at least one general characteristic of the subject for the plurality of sites on the subject, and for analyzing the electrical activity and determining therefrom analysis values for a plurality of muscles, each of the plurality of muscles corresponding to a respective one of the plurality of sites, wherein determining analysis values comprises factoring the adipose thickness factors into the measured electrical activity;
   the processor determining the adipose thickness factors by applying a formula that includes a set of coefficients, each coefficient relating to one of the plurality of sites on the subject.

18. A system for determining muscle dysfunction of a subject, the system comprising:
   (a) a plurality of electrical activity sensors for making electrical activity measurements for a respective plurality of sites on the subject; and
   (b) a processor for analyzing the electrical activity measurements and determining therefrom analysis values for each of a plurality of muscles, and determining for each of the plurality of muscles a degree of departure from a normal condition by normalizing the analysis values with respect to the plurality of muscles, wherein the normal condition is an ideal normal condition.

19. A system for determining muscle dysfunction of a subject, the system comprising:
   (a) a plurality of electrical activity sensors for making electrical activity measurements for a respective plurality of sites on the subject; and (b) a processor for analyzing the electrical activity measurements and determining therefrom analysis values for each of a plurality of muscles, and determining for each of the plurality of muscles a degree of departure from a normal condition by normalizing the analysis values with respect to the plurality of muscles;

the plurality of electrical activity sensors making electrical activity measurements during specific periods in the execution of a set of motor tasks, and the processor determining the degree of departure by selectively integrating the analysis values across the set of motor tasks.

20. A system for determining muscle dysfunction of a subject, the system comprising:

(a) a plurality of electrical activity sensors for making electrical activity measurements for a respective plurality of sites on the subject; and (b) a processor for analyzing the electrical activity measurements and determining therefrom analysis values for each of a plurality of muscles, and determining for each of the plurality of muscles a degree of departure from a normal condition by normalizing the analysis values with respect to the plurality of muscles;

the electrical activity measurements relating to a performance of a motor task, and the processor determining a set of relationships for each of the analysis values, each relationship relating the analysis value to one of the other analysis values as a pair, and the processor determining the degree of departure by selectively integrating across the set of relationships.

21. The system of claim 20, the processor factoring into each relationship a weighting factor that reflects a biomechanical significance for the performance of the motor task correlating the muscles associated with the pair of analysis values.

22. The system of claim 20, the processor factoring into each relationship a weighting factor that reflects a biomechanical significance that correlates the motor task and the one of the plurality of muscles associated with the analysis value.

23. The system of claim 20, the processor factoring into each relationship a factor that reflects a systematic variability in measurement of electrical activity.

24. A computer readable medium having stored therein one or more sequences of instructions for analyzing for muscle dysfunction of a subject, said one or more sequences of instructions causing one or more processors to perform a plurality of acts, said acts comprising:

(a) calculating adipose thickness factors for a predetermined plurality of sites on the subject; and (b) analyzing electrical activity measurements and determining therefrom analysis values for a plurality of muscles, each of the plurality of muscles corresponding to a respective one of the plurality of sites, and in determining the analysis values, factoring the adipose thickness factors into the electrical activity measurements;

the adipose thickness factors being determined by applying results of obtained measurements from a sampling of individuals, the results relating adipose thickness to general characteristics measured for the individuals, the at least one general characteristic of the subject corresponding to at least one of the general characteristics measured for the individuals; the results being represented in a set of coefficients that are applied to a formula, each coefficient relating to one of the at least one general characteristic of the subject and to one site of the plurality of sites on the subject;

the formula having a form:

$$\text{Adipose} = B_0 + B_1 X_1 + \ldots + B_n X_n,$$

wherein $B_0$ through $B_n$ comprise the set of coefficients for a given site, $X_1$ through $X_n$ represent values for a different one of the at least one general characteristic of the subject, and n is the number of the at least one general characteristic.

25. A computer readable medium having stored therein one or more sequences of instructions for analyzing for muscle dysfunction of a subject, said one or more sequences of instructions causing one or more processors to perform a plurality of acts, said acts comprising:

(a) calculating adipose thickness factors for a predetermined plurality of sites on the subject; and (b) analyzing electrical activity measurements and determining therefrom analysis values for a plurality of muscles, each of the plurality of muscles corresponding to a respective one of the plurality of sites, and in determining the analysis values, factoring the adipose thickness factors into the electrical activity measurements;

the adipose thickness factors being determined by applying results of obtained measurements from a sampling of individuals, the results relating adipose thickness to general characteristics measured for the individuals, the at least one general characteristic of the subject corresponding to at least one of the general characteristics measured for the individuals, the results being represented in a set of coefficients that are applied to a formula, each coefficient relating to one of the at least one general characteristic of the subject and to one site of the plurality of sites on the subject, wherein the coefficients are regression-based coefficients.

26. A computer readable medium having stored therein one or more sequences of instructions for analyzing for muscle dysfunction of a subject, said one or more sequences of instructions causing one or more processors to perform a plurality of acts, said acts comprising:

(a) calculating adipose thickness factors for a predetermined plurality of sites on the subject; and (b) analyzing electrical activity measurements and determining therefrom analysis values for a plurality of muscles, each of the plurality of muscles corresponding to a respective one of the plurality of sites, and in determining the analysis values, factoring the adipose thickness factors into the electrical activity measurements;

the adipose thickness factors being determined by applying results of obtained measurements from a sampling of individuals, the results relating adipose thickness to general characteristics measured for the individuals, the at least one general characteristic of the subject corresponding to at least one of the general characteristics measured for the individuals, the results being represented in a set of coefficients that are applied to a formula, each coefficient relating to one of the at least one general characteristic of the subject and to one site of the plurality of sites on the subject, the one of the set of general characteristics of the subject being a gender, a height, a weight, a Body Mass Index, a body type, a waist circumference, a chest circumference, a wrist circumference, or a light transmissiveness of skin.

27. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject; and
   (b) analyzing electrical activity measurements and determining therefrom analysis values for a plurality of muscles, each of the plurality of muscles corresponding to a respective one of the plurality of sites, and in determining the analysis values, factoring the adipose thickness factors into the electrical activity measurements;
      the adipose thickness factors being determined by applying a formula that includes a set of coefficients, each coefficient relating to one of the plurality of sites on the subject.

28. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject;
   (b) determining analysis values for each of a plurality of muscles from electrical activity measurements for the plurality of sites; and
   (c) determining from the analysis values, a degree of departure from a normal condition, the degree of departure being normalized with respect to the plurality of muscles, wherein the normal condition is an ideal normal condition.

29. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject;
   (b) determining analysis values for each of a plurality of muscles from electrical activity measurements for the plurality of sites; and
   (c) determining from the analysis values, a degree of departure from a normal condition, the degree of departure being normalized with respect to the plurality of muscles;
      wherein the electrical activity measurements are previously made at the plurality of sites are for specific periods in the execution of a set of motor tasks, and the degree of departure is determined by selectively integrating the analysis values across the set of motor tasks.

30. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject;
   (b) determining analysis values for each of a plurality of muscles from electrical activity measurements for the plurality of sites; and
   (c) determining from the analysis values, a degree of departure from a normal condition, the degree of departure being normalized with respect to the plurality of muscles;
      the electrical activity measurements relating to a performance of a motor task, and said acts further comprise determining a set of relationships for each of the analysis values, each relationship in the set for an analysis value relating the analysis value to one of the other muscle analysis values as a pair, and the degree of departure being determined by selectively integrating across the set of relationships.

31. The computer readable medium of claim 30, each relationship including a weighting factor that reflects a biomechanical significance in the execution of a motor task correlating the muscles associated with the pair of analysis values.

32. The computer readable medium of claim 30, each relationship including a weighting factor that reflects a biomechanical significance that correlates the motor task with the one of the plurality of muscles associated with the analysis value.

33. The computer readable medium of claim 30, each relationship including a factor that reflects a systematic variability in measurement of electrical activity.

34. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject;
   (b) determining analysis values for each of a plurality of muscles from electrical activity measurements for the plurality of sites; and
   (c) determining from the analysis values, a degree of departure from a normal condition, the degree of departure being normalized with respect to the plurality of muscles;
      wherein the degree of departure comprises a continuous measure.

35. A computer readable medium having stored therein one or more sequences of instructions for analyzing for muscle dysfunction of a subject, said one or more sequences of instructions causing one or more processors to perform a plurality of acts, said acts comprising:
   (a) calculating adipose thickness factors for a predetermined plurality of sites on the subject;
   (b) determining analysis values for each of a plurality of muscles from electrical activity measurements for the plurality of sites; and
   (c) determining from the analysis values, a degree of departure from a normal condition, the degree of departure being normalized with respect to the plurality of muscles;
      wherein said acts further comprise calculating adipose thickness factors for the plurality of sites, and in determining the analysis values, factoring in the adipose thickness factors.

36. A back muscle dysfunction evaluation network for determining muscle dysfunction of subjects comprising:
   (a) at least one data collection system for making electrical activity measurements at a respective plurality of sites on each of the subjects;
   (b) a data analysis system for analyzing the electrical activity measurements and determining therein analysis values for a plurality of muscles, each of the plurality of muscles corresponding to a respective one of the plurality of sites; and (c) a communications link linking the data analysis system and the data collection system, for transmitting the electrical activity measurements of subjects to the data analysis system.

37. The back muscle dysfunction evaluation network of claim 36, the data analysis system comprising a processor and sample database, the processor using the sample database to determine the analysis values for the plurality of muscles and to analyze the analysis values.

38. The back muscle dysfunction evaluation network of claim 36, the data analysis system producing a report on a degree of departure from a normal condition for each of the plurality of muscles, and the communications link transmitting the report to the data collection system.

39. The back muscle dysfunction evaluation network of claim 38, wherein the degree of departure for the analysis values is normalized with respect to the plurality of muscles.

40. The back muscle dysfunction evaluation network of claim 36, the data collection system making a measurement of at least one general characteristic of each subject, the communications link transmitting the measurement of the at least one general characteristic to the data analysis system, and the data analysis system determining adipose thickness factors for the plurality of sites on the subject based on the at least one general characteristic of each subject, and in determining analysis values, factoring the adipose thickness factors into the electrical activity measurements.

41. The back muscle dysfunction evaluation network of claim 40, the at least one general characteristic of each subject being a gender, a height, a weight, a Body Mass Index, a body type, a waist circumference, a chest circumference, a wrist circumference, or a light transmissiveness of skin.

42. The back muscle dysfunction evaluation network of claim 36, the communications link is an Internet connection.

43. A muscle dysfunction report comprising:

(a) a reference to a tested muscle; and (b) an impairment value representing a degree of departure of the muscle from an ideal normal condition, wherein the ideal normal condition represents a specific state or condition within a normal range, wherein different muscles having the same degree of departure have the same impairment values, and wherein the impairment value relates to an impairment index capable of characterizing any degree of departure of the muscle from an ideal normal condition.

* * * * *